(12) United States Patent
Ahn et al.

(10) Patent No.: US 11,497,400 B2
(45) Date of Patent: Nov. 15, 2022

(54) HYBRID IMAGING SYSTEM FOR PHOTODIAGNOSIS AND PHOTOTHERAPY

(71) Applicant: KOREA PHOTONICS TECHNOLOGY INSTITUTE, Gwangju (KR)

(72) Inventors: Jaesung Ahn, Gwangju (KR); Hyeong Ju Park, Gwangju (KR); Anjin Park, Seoul (KR); Joo Beom Eom, Gwangju (KR); Jonghyun Eom, Gwangju (KR); Hong Lyel Jung, Gwangju (KR)

(*) Notice: Subject to any disclaimer, the term of this patent is extended or adjusted under 35 U.S.C. 154(b) by 455 days.

(21) Appl. No.: 16/610,533

(22) PCT Filed: Nov. 30, 2018

(86) PCT No.: PCT/KR2018/015091
§ 371 (c)(1),
(2) Date: Nov. 4, 2019

(87) PCT Pub. No.: WO2019/164102
PCT Pub. Date: Aug. 29, 2019

(65) Prior Publication Data
US 2020/0085304 A1    Mar. 19, 2020

(30) Foreign Application Priority Data
Feb. 20, 2018    (KR) .................. 10-2018-0019877

(51) Int. Cl.
*A61B 5/00*    (2006.01)
*A61B 5/01*    (2006.01)
(Continued)

(52) U.S. Cl.
CPC .......... *A61B 5/0036* (2018.08); *A61B 5/0077* (2013.01); *A61B 5/015* (2013.01);
(Continued)

(58) Field of Classification Search
CPC ...... G01N 21/359; A61B 5/015; A61B 5/062; A61B 5/0059; A61B 5/007; A61N 5/062; A61N 2005/0659; A61N 2005/0663
See application file for complete search history.

(56) References Cited

U.S. PATENT DOCUMENTS

2005/0002021 A1* 1/2005 Kreh ................ G01N 21/8806
356/237.2
2005/0182295 A1* 8/2005 Soper .................... A61B 5/062
600/117
(Continued)

FOREIGN PATENT DOCUMENTS

JP    2003-339648 A    12/2003
KR    10-1392132 B1    4/2009
(Continued)

OTHER PUBLICATIONS

Fahlgren "Lights, camera, action: high-throughput plant phenotyping is ready for a close-up", Current Opinion in Plant Biology 2015, 24:93-99 (Year: 2015).*
(Continued)

*Primary Examiner* — Oommen Jacob

(57) ABSTRACT

The present invention relates to a hybrid imaging system for photodiagnosis and phototherapy and, more particularly, to a hybrid imaging system for photodiagnosis and phototherapy, which simultaneously acquires a visible ray image or a near-infrared ray image and a lonq wave infrared ray image by using an optical method. The hybrid imaging system for photodiagnosis and phototherapy according to the present invention includes a light distribution unit, a visible ray/near-infrared ray measurement unit, a long wave infrared ray measurement unit, and a light source unit, thereby simultaneously and quickly extracting a visible ray
(Continued)

image, a near-infrared ray image, and a long wave infrared ray image without mutual distortion.

7 Claims, 8 Drawing Sheets

(51) Int. Cl.
    *A61N 5/06*     (2006.01)
    *G02B 5/20*     (2006.01)
    *G02B 13/14*     (2006.01)
    *G02B 27/14*     (2006.01)

(52) U.S. Cl.
    CPC ............. *A61N 5/062* (2013.01); *G02B 5/208* (2013.01); *G02B 13/14* (2013.01); *G02B 27/142* (2013.01); *A61N 2005/0659* (2013.01); *A61N 2005/0663* (2013.01)

(56) References Cited

U.S. PATENT DOCUMENTS

| | | | | |
|---|---|---|---|---|
| 2008/0014654 A1* | 1/2008 | Weisman | ........... | G01N 21/6402 |
| | | | | 436/171 |
| 2009/0039255 A1* | 2/2009 | Andrews | ................ | G01N 21/35 |
| | | | | 250/301 |
| 2009/0137908 A1* | 5/2009 | Patwardhan | ........... | A61B 5/444 |
| | | | | 600/476 |
| 2009/0270678 A1* | 10/2009 | Scott | .................... | A61B 90/361 |
| | | | | 600/109 |
| 2009/0326383 A1* | 12/2009 | Barnes | .................. | A61B 5/442 |
| | | | | 850/1 |
| 2011/0144462 A1 | 6/2011 | Lifsitz et al. | | |
| 2011/0152692 A1* | 6/2011 | Nie | ...................... | A61B 90/361 |
| | | | | 600/473 |
| 2013/0322729 A1* | 12/2013 | Mestha | ................. | G06T 7/0016 |
| | | | | 382/134 |
| 2014/0276008 A1* | 9/2014 | Steinbach | ........... | A61B 5/0059 |
| | | | | 600/424 |
| 2017/0205607 A1* | 7/2017 | Li | ............................ | G02B 9/04 |
| 2020/0085304 A1* | 3/2020 | Ahn | ..................... | G02B 27/142 |

FOREIGN PATENT DOCUMENTS

| | | |
|---|---|---|
| KR | 10-2010-0039170 A | 4/2010 |
| KR | 10-2014-0028358 A | 3/2014 |
| KR | 10-1647022 B1 | 8/2016 |

OTHER PUBLICATIONS

JP2003339648A English translation (Year: 2003).*
International Search Report for PCT/KR2018/015091 dated Feb. 7, 2019.

* cited by examiner

HYBRID IMAGING SYSTEM FOR PHOTODIAGNOSIS AND PHOTOTHERAPY

CROSS REFERENCE TO RELATED APPLICATIONS

This application claims priority to Korean Patent Application No. 10-2018-0019877, filed on Feb. 2, 2018. Further, the application is the National Phase application of International Application No. PCT/KR2018/015091, filed on Nov. 30, 2018, which designates the United States. Each of these applications is hereby incorporated by reference in their entirety into the present application.

TECHNICAL FIELD

The present invention relates to a hybrid imaging system for photodiagnosis and phototherapy and, more particularly, to a hybrid imaging system for photodiagnosis and phototherapy, which simultaneously acquires a visible ray image or a near-infrared ray image and a long wave infrared ray image by using an optical method.

BACKGROUND ART

Recently, diagnosis and therapy methods using various optical methods for precision diagnosis and treatment of cancer have been developed. There are advantages that the photodiagnosis of tumor tissue allows precise real-time imaging of time tumor tissue in comparison with the diagnosis of cancer through existing blood tests and tissue biopsy, and the phototherapy allows precise minimally invasive treatment in comparison with existing surgery, chemotherapy, radiation therapy, immunotherapy, and gene therapy.

Among technologies using various optical methods, in the field of cancer diagnosis, a technique of precisely tracking the tumor tissue using the near-infrared fluorescence signal has proved its diagnostic effectiveness, and research for clinical application has been actively conducted. Also, regarding cancer treatment, it has been reported that a phototherapy technique is performed in a manner a photosensitizer is administered to a tumor tissue site and irradiated with light of a specific wavelength, thereby inducing heat dissipation or active oxygen generation and thus necrotizing the tumor tissue.

However, due to mutual distortion between the visible ray image and the near-infrared ray image, and the long wave infrared ray image, there is a problem that the photodiagnosis technique and the phototherapy technique cannot be performed at the same time.

DOCUMENT OF RELATED ART

Patent Document

Korean Patent Registration No. 10-1392132 (Registered on May 19, 2014)

DISCLOSURE

Technical Problem

Accordingly, the present invention has been made to solve the above-mentioned problems occurring in the related art, and it is an objective of the present invention to simultaneously extract a visible ray image, a near-infrared ray image, and a long wave infrared ray image by an optical method. In addition, the object of the present invention is such that the visible ray image, the near-infrared ray image, and the long wave infrared ray image have no mutual distortion so that the photodiagnosis and the phototherapy for the tumor tissue can be quickly and easily performed at the same time.

It is another object of the present invention to enable real-time simultaneous tracking for photodiagnosis and phototherapy of tumor tissues, which have been individually performed in the related art, thereby enabling precise and efficient tumor treatment.

Technical Solution

In order to achieve the above objects, a hybrid imaging system for photodiagnosis and phototherapy according to the present invention may include a light distribution unit, a visible ray/near-infrared ray measurement unit, a long wave infrared ray measurement unit, and a light source unit The light source unit may irradiate the object with near-infrared rays or long wave infrared rays having a predetermined wavelength. The light distribution unit may transmit or reflect an optical signal generated according to a light source irradiated to the object from the light source unit to be distributed into a visible optical signal and a near-infrared optical signal, and a long wave infrared optical signal. Further, the light distribution unit may include a transmissive layer through which the visible optical signal and the near-infrared optical signal of a predetermined wavelength are transmitted, and a long wave infrared ray reflective layer by which the long wave infrared optical signal is reflected.

The visible ray/near-infrared ray measurement unit may receive and selectively filter the visible optical signal and the near-infrared optical signal distributed from the light distribution unit, to measure at least one of the visible optical signal and the near-infrared optical signal. Further, the visible ray/near-infrared ray measurement unit may include a near-infrared ray cut-off filter, a filter slide mount, an imaging lens, and a visible ray/near-infrared ray camera.

The near-infrared ray cut-off filter is provided at a front end of the visible ray/near-infrared ray measurement unit into which the optical signal is incident to selectively transmit only the near-infrared optical signal.

The filter slide mount may control an operation of the near-infrared cut-off filter.

In addition, the imaging lens may form an image of the visible optical signal and/or the near-infrared optical signal. The visible ray/near-infrared ray camera may measure the optical signal of which the image is formed through the imaging lens to extract a visible ray image and/or a near-infrared ray image.

The long wave infrared ray measurement unit may receive and measure the long wave infrared optical signal distributed from the light distribution unit. In addition, the long wave infrared ray measurement unit may include a long wave infrared imaging lens receiving the long wave infrared optical signal distributed from the light distribution unit to form an image thereof, and a long wave infrared ray camera measuring the long wave infrared optical signal of which an image is formed through the long wave infrared imaging lens to extract the long wave infrared ray image.

Advantageous Effects

As described above, in the hybrid imaging system for photodiagnosis and phototherapy according to the present invention, there is an advantage that a visible ray image, a near-infrared ray image, and a long wave infrared ray image are extracted at the same time from the measurement object, so that distortion due to a difference in photographing angles between images does not occur. In addition, there is an effect that it is possible to implement a visible ray/near-infrared ray fusion image, a visible ray/long wave infrared ray fusion image, or a near-infrared ray/long wave infrared ray fusion image, and perform an analysis on the fusion images, without a separate correction for image distortion.

In addition, there is an effect that real-time simultaneous tracking is enabled for photodiagnosis and phototherapy of tumor tissues, which have been individually performed in the related art, thereby enabling precise and efficient tumor treatment.

BEST MODE

Figure 1A:
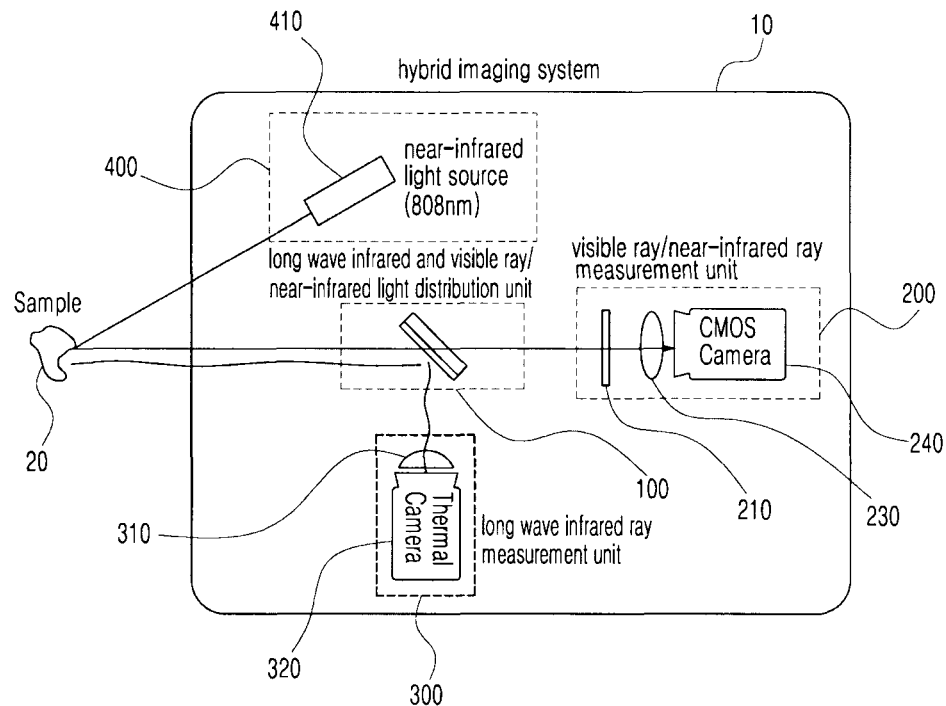
FIG. 1A is a general view illustrating a hybrid imaging system for photodiagnosis and phototherapy according to an embodiment of the present invention.

Hereinafter, embodiments of the present invention will be described in detail with reference to the accompanying drawings so that those skilled in the art can easily carry out the present invention. The present invention may, however, be embodied in many different forms and should not be construed as limited to the embodiments set forth herein. In order to clearly illustrate the present invention, parts not related to the description are omitted, and similar parts are denoted by similar reference characters throughout the specification.

Throughout the specification, when an element is referred to as "comprising" a component, it means that the element can include other components as well, without excluding other components unless specifically stated otherwise. Also, the terms "part", "module", and the like described in the specification mean units for processing at least one function or operation, and may be implemented by hardware or software, or a combination of hardware and software.

Hereinafter, the present invention will be described in detail with reference to the preferred embodiments of the present invention referring to the accompanying drawings.

Like reference symbols in the drawings denote like elements.

Figure 1B:
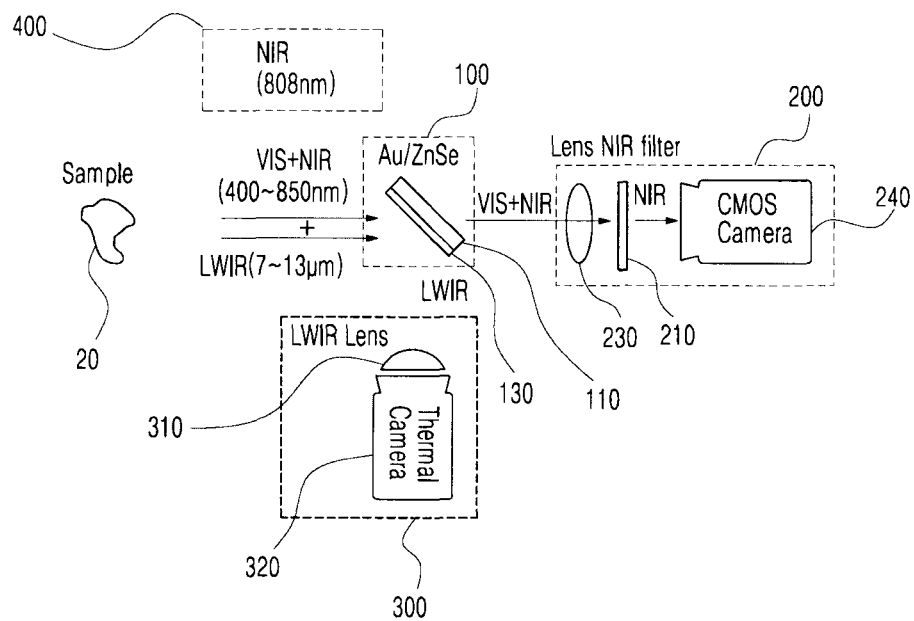
FIG. 1B is a view illustrating the movement paths of visible rays and near-infrared rays, and long wave infrared rays in the hybrid imaging system for photodiagnosis and phototherapy according to an embodiment of the present invention.

FIG. 1 is a view illustrating a concept of a hybrid imaging system for photodiagnosis and phototherapy according to an embodiment of the present invention. FIG. 1A is a general view illustrating a hybrid imaging system for photodiagnosis and phototherapy according to an embodiment of the present invention. FIG. 1B is a view illustrating the movement paths of visible rays and near-infrared rays, and long wave infrared rays in the hybrid imaging system for photodiagnosis and phototherapy according to an embodiment of the present invention.

Figure 2:
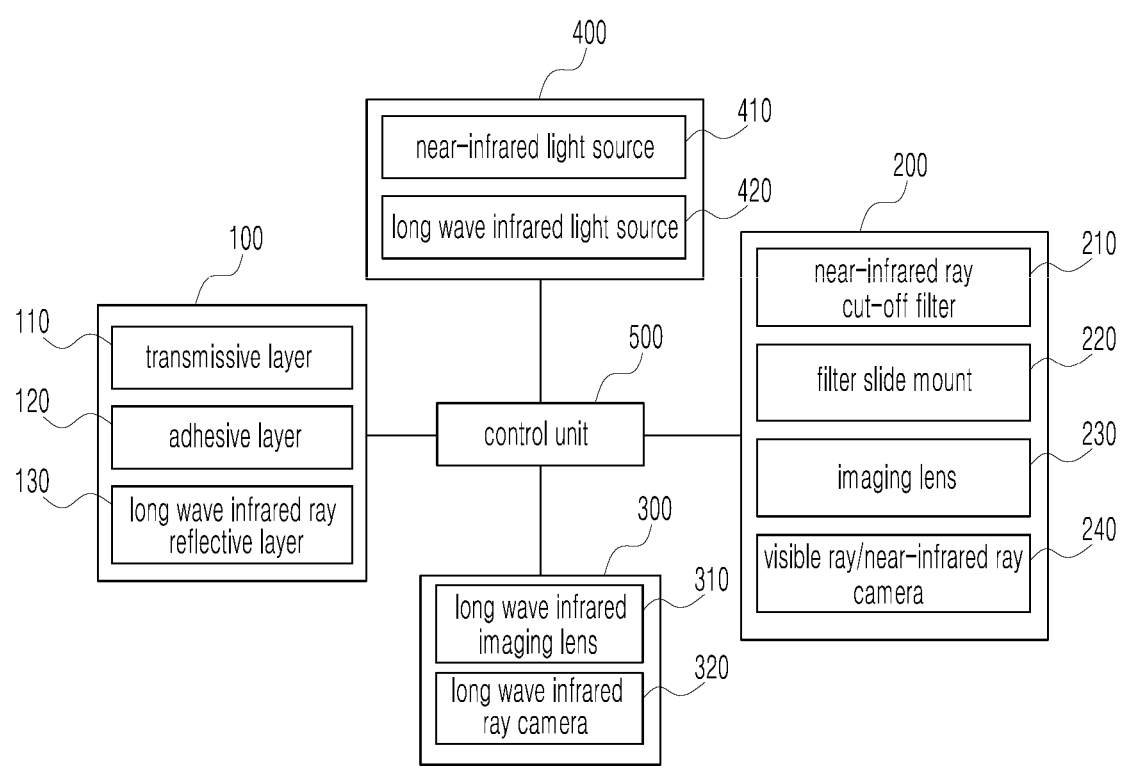
FIG. 2 is a view showing a configuration of a hybrid imaging system for photodiagnosis and phototherapy according to an embodiment of the present invention.
Figure 3:
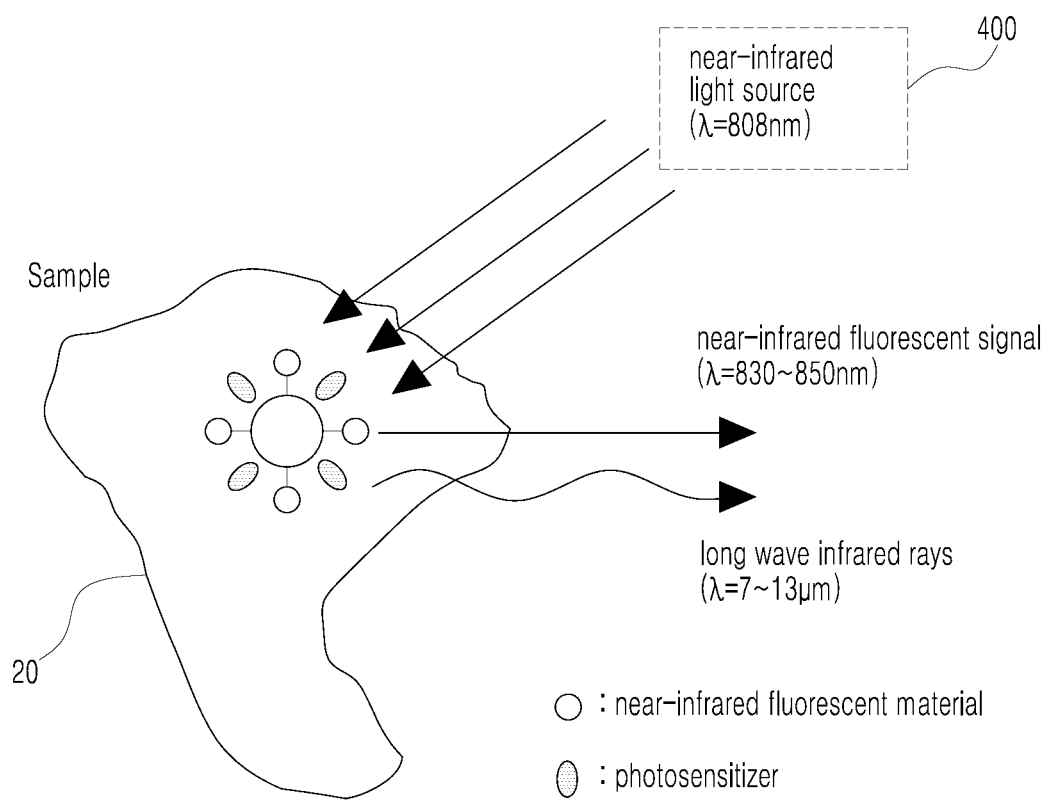
FIG. 3 is a view illustrating a process of applying a photothermal therapy technique using particles having a photosensitizer and a near-infrared fluorescent material to an object, and an optical signal generated according to irradiation of a near-infrared light source.

In addition, FIG. 2 is a view showing a configuration of a hybrid imaging system for photodiagnosis and phototherapy according to an embodiment of the present invention, and FIG. 3 is a view illustrating a process of applying a photothermal therapy technique using particles having a photosensitizer and a near-infrared fluorescent material to an object, and an optical signal generated according to irradiation of a near-infrared light source.

The present invention relates to a hybrid imaging system for photodiagnosis and phototherapy that simultaneously extracts a visible ray image and a near-infrared ray (NIR) image, and a long wave infrared ray (LWIR) image using an optical method. Namely, the near-infrared ray image is analyzed on the basis of a near-infrared fluorescence signal to perform cancer diagnosis by precisely tracking the tumor tissue in real time, and at the same time, the long wave infrared ray image is analyzed on the basis of a long wave infrared ray photosensitizer to monitor the phototherapeutic effect on tumor tissue by tracking the heat dissipation of the photosensitizer.

As shown in FIG. 3, the hybrid imaging system 10 according to an embodiment of the present invention analyzes a visual ray image of the object 20 and a near-infrared ray image of the object 20 to monitor near-infrared ray fluorescent material of the object 20, and at the same time analyzes the near-infrared ray image to monitor the heat dissipation of the photosensitizer, in order to simultaneously perform photodiagnosis and phototherapy on the tumor tissue of the object 20.

The hybrid imaging system 10 according to an embodiment of the present invention includes a light distribution unit 100, a visible ray/near-infrared ray measurement unit 200, a long wave infrared ray measurement unit 300, a light source unit 400, and a control unit 500.

Figure 4:
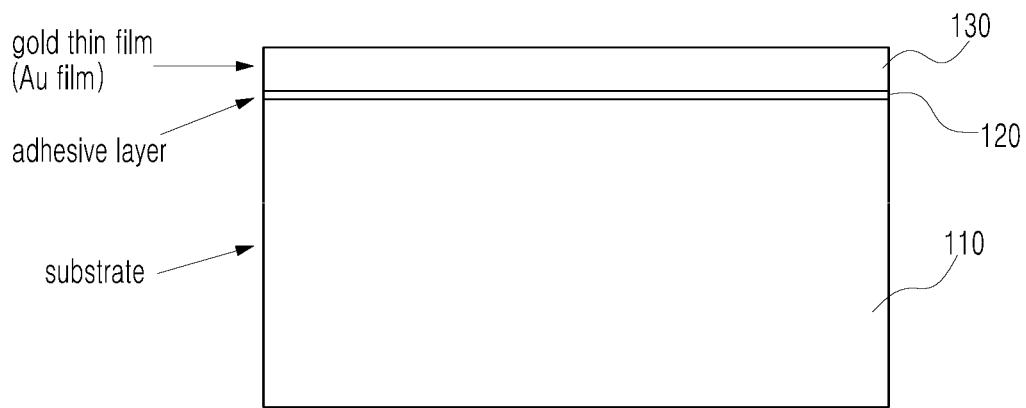
FIG. 4 is a view illustrating a structure of a light distribution unit in a hybrid imaging system for photodiagnosis and phototherapy according to an embodiment of the present invention.
Figure 5:
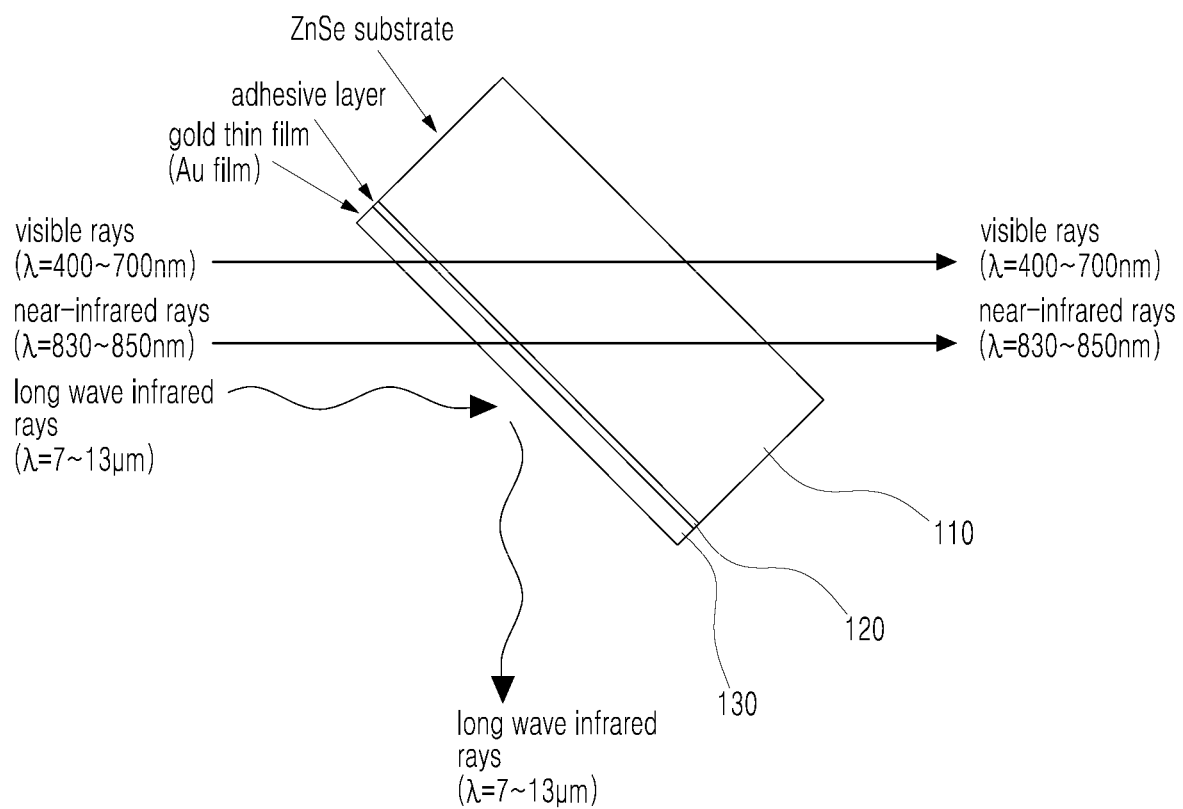
FIG. 5 is a view illustrating that optical signals are distributed using the light distribution unit 100 of FIG. 4.

FIG. 4 is a view illustrating a structure of a light distribution unit in a hybrid imaging system for photodiagnosis and phototherapy according to an embodiment of the present invention, and FIG. 5 is a view illustrating that optical signals are distributed using the light distribution unit 100 of FIG. 4.

The light distribution unit 100 converts an optical signal generated according to a light source irradiated on the object 20 by the light source unit 400 into a visible optical signal, a near-infrared optical signal, and a long wave infrared optical signal. In addition, the light distribution unit 100 may include a transmissive layer 110 through which the visible rays and the near-infrared rays are transmitted and a long wave infrared ray reflective layer 130 by which the long wave infrared rays are reflected. In addition, an adhesive layer 120 may be formed between the transmissive layer 110 and the long wave infrared ray reflective layer 130 so as to allow the transmissive layer 110 and the long wave infrared ray reflective layer 130 to adhere to each other.

Here, the transmissive layer 110 may be a substrate comprised zinc selenide (ZnSe). In addition, both sides of the substrate may be coated so that visible rays and near-infrared rays having a wavelength of 400 to 850 nm are transmitted in an anti-reflection manner.

In addition, the adhesive layer 110 is deposited to a thickness of 1 to 10 nanometers (nm), and may be comprised indium tin oxide (ITO) or titanium.

In addition, the long wave infrared ray reflective layer 130 may be deposited as a metal thin film having a thickness of 100 to 500 nanometers (nm), and comprised a metal having high long wave infrared reflection, such as gold or platinum.

The light distribution unit 100 according to an embodiment of the present invention includes a long wave infrared ray reflective layer 130 through which the visible rays and the near-infrared rays are transmitted and by which the long wave infrared rays are reflected.

Figure 6A:
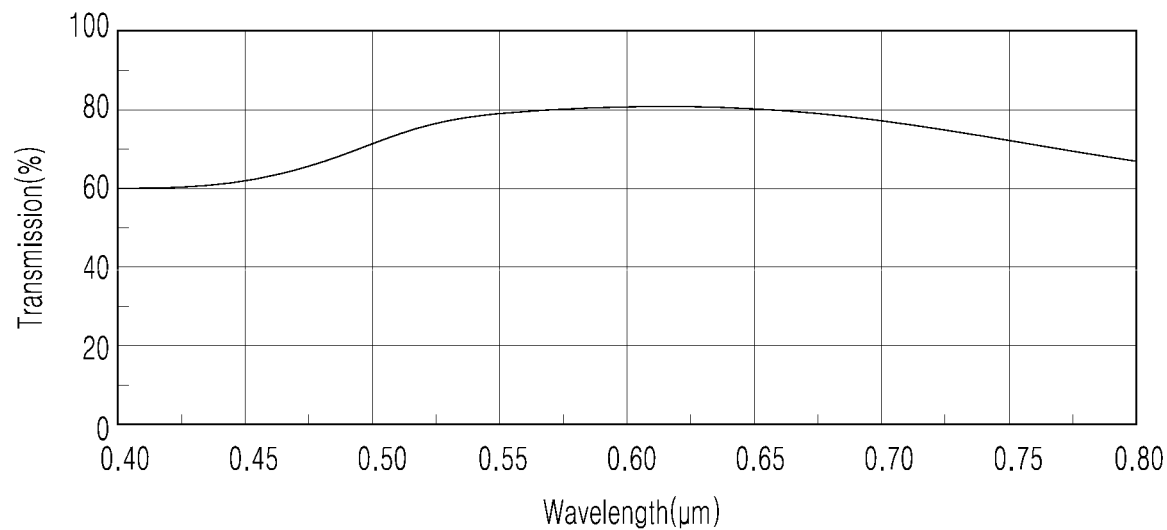
FIG. 6A is a view illustrating a spectrum of visible ray and near-infrared ray wavelengths transmitted by the light distribution unit 100 according to an embodiment of the present invention.
Figure 6B:
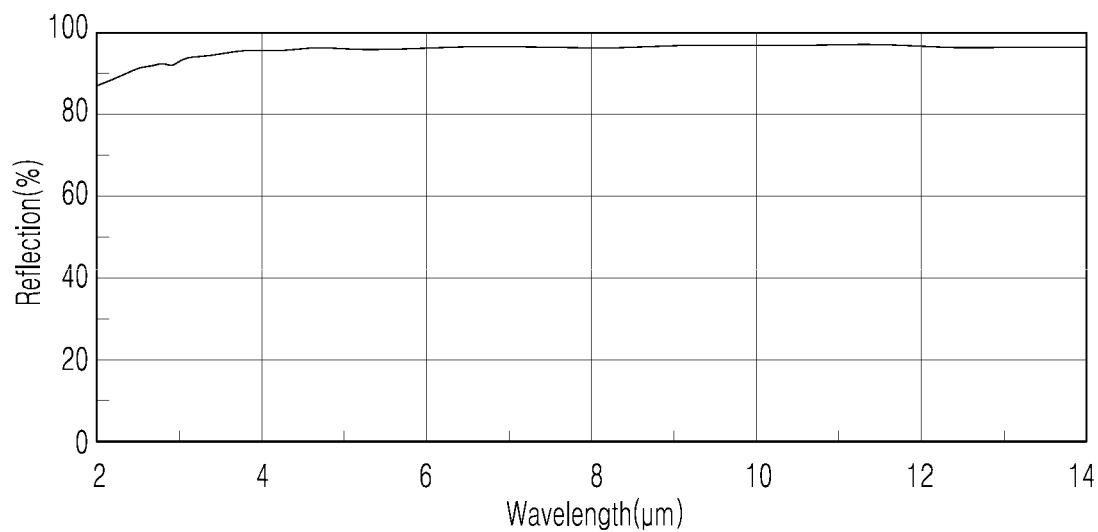
FIG. 6B is a view illustrating a spectrum of infrared ray wavelengths reflected by a light distribution unit 100 according to an embodiment of the present invention.

FIG. 6 is a diagram showing a transmission spectrum of visible ray/near-infrared rays and a reflection spectrum of long wave infrared rays, which are distributed through the light distribution unit 100 of FIG. 5. FIG. 6A is a view illustrating a spectrum of visible and near-infrared ray wavelengths transmitted by the light distribution unit 100 according to an embodiment of the present invention, and FIG. 6B is a view illustrating a spectrum of infrared ray wavelengths reflected by a light distribution unit 100 according to an embodiment of the present invention.

The thickness of the metal thin film of the long wave infrared ray reflective layer 130 is preferably set to exhibit a performance having a transmission of 60% or more in the case of visible rays and near-infrared rays having a wavelength of 400 to 850 nanometers and a reflection of 95% or more in the case of long wave infrared rays having a wavelength of 7 to 13 micrometers.

Figure 7:
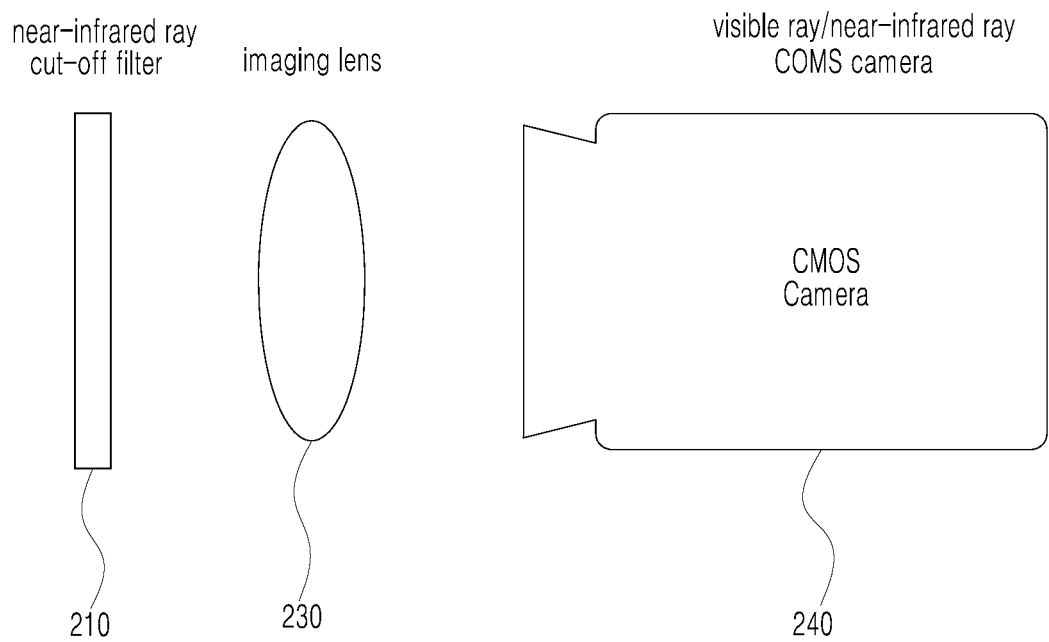
FIG. 7 is a view illustrating a visible ray/near-infrared ray measurement unit in a hybrid imaging system for photodiagnosis and phototherapy according to an embodiment of the present invention.
Figure 8:
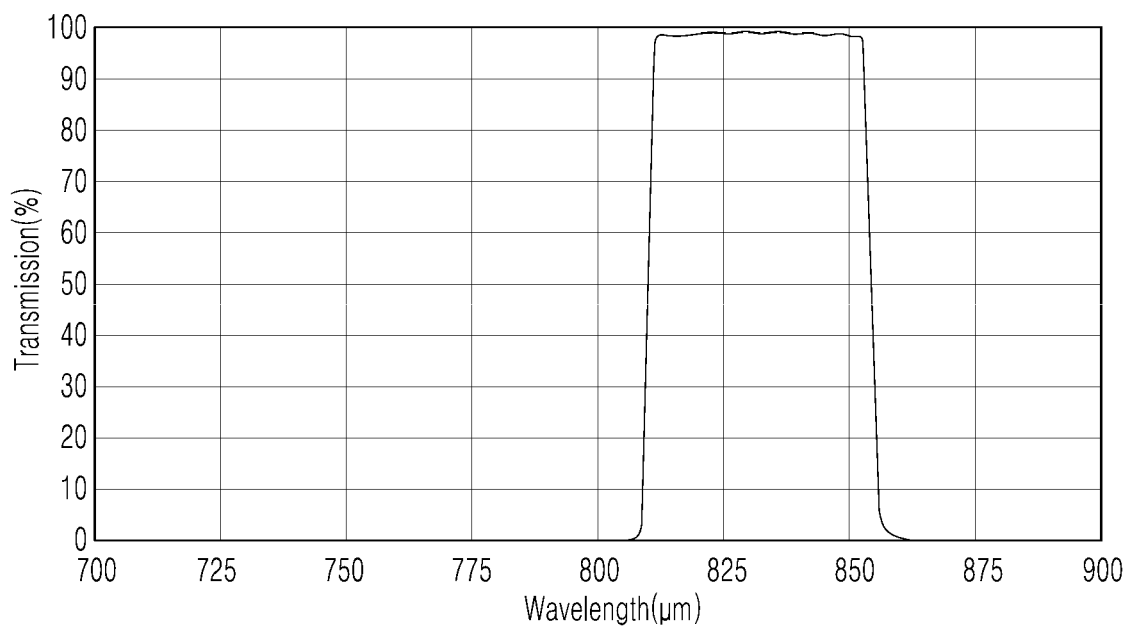
FIG. 8 is a view illustrating a spectrum of a near-infrared ray transmitted through the near-infrared cut-off filter of FIG. 7.

FIG. 7 is a view illustrating a visible ray/near-infrared ray measurement unit 200 in a hybrid imaging system for photodiagnosis and phototherapy according to an embodiment of the present invention, and FIG. 8 is a view illustrating a spectrum of a near-infrared ray transmitted through the near-infrared cut-off filter of FIG. 7.

Figure 9A:
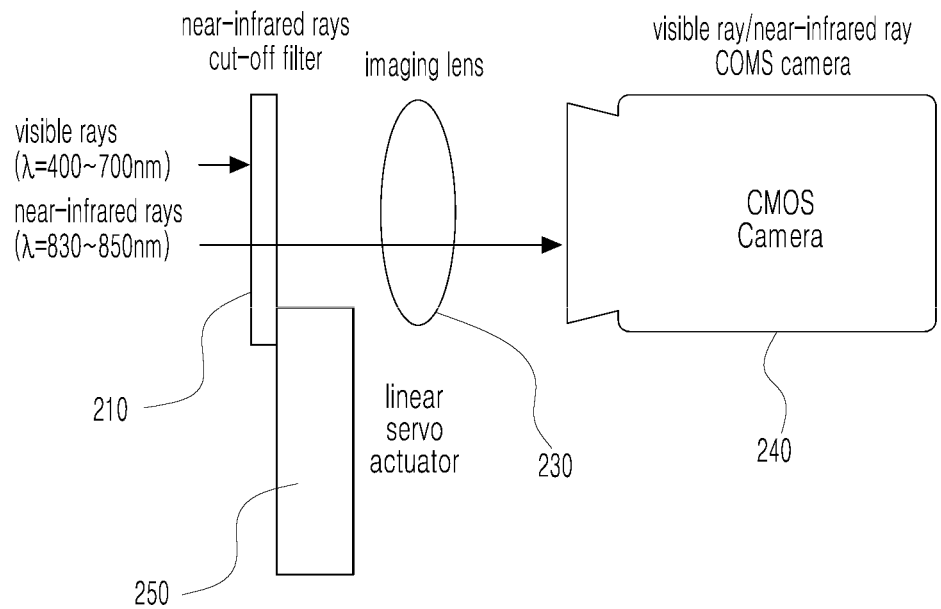
FIG. 9A is a view illustrating that a near-infrared ray cut-off filter 210 is disposed so that a visible optical signal is filtered and only a near-infrared optical signal is transmitted.
Figure 9B:
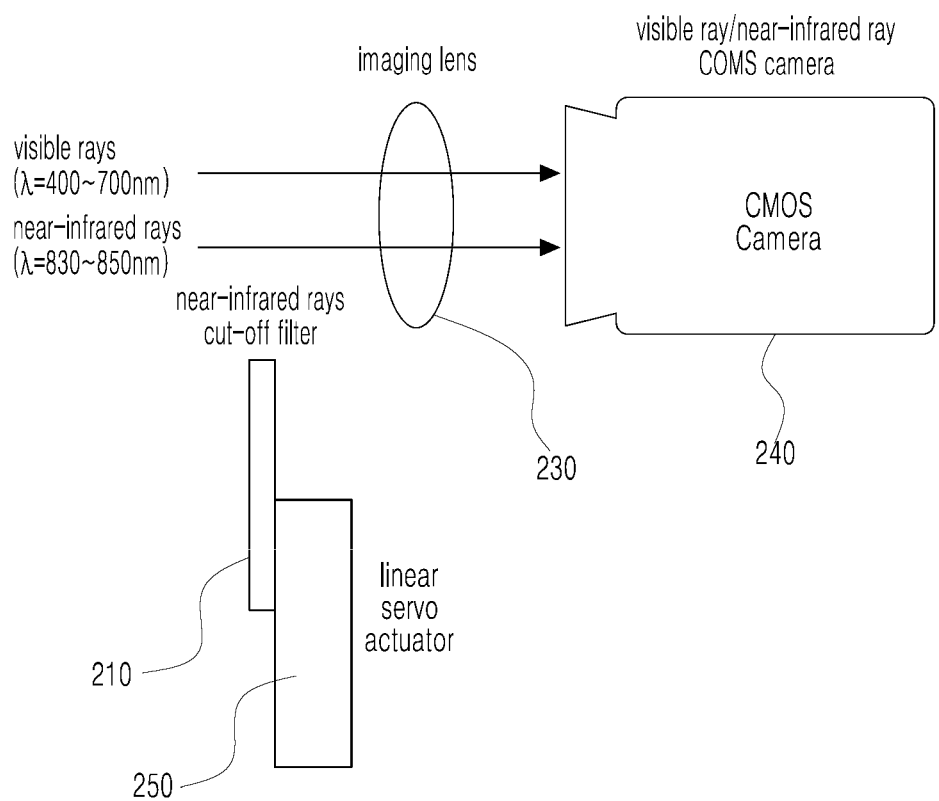
FIG. 9B is a view illustrating a near-infrared cut-off filter 210 is removed so that the visible optical signal and the near-infrared optical signal are transmitted at the same time.

FIG. 9 is a view illustrating the operation of the visible ray/near-infrared ray measurement unit 200 of FIG. 7. FIG. 9A is a view illustrating that a near-infrared ray cut-off filter 210 is disposed so that a visible optical signal is filtered and only a near-infrared optical signal is transmitted, and FIG. 9B is a view illustrating a near-infrared cut-off filter 210 is removed so that the visible optical signal and the near-infrared optical signal are transmitted at the same time.

The visible/near-infrared ray measurement unit 200 may measure a visible optical signal and a near-infrared optical signal that transmits through the light distribution unit 100. Also, the visible ray/near-infrared ray measurement unit 200 includes a near-infrared cutoff filter 210, a filter slide mount 220, an imaging lens 230, and a visible ray/near-infrared ray camera 240.

The near-infrared ray cut-off filter 210 is provided on the front side of the visible ray/near-infrared ray measurement unit 200 to selectively transmit only the near-infrared rays. The near-infrared cut-off filter 210 is comprised so that materials having different refractive indexes are alternately and continuously deposited on a glass substrate, and at least 90 percent (%) of the near-infrared rays having a wavelength between 820 and 850 nanometers (nm) are transmitted.

In addition, the near-infrared cut-off filter 210 is attached to the actuator 250 driven by an electrical signal and is disposed in a direction perpendicular to the optical signal acquisition path of the visible ray/near-infrared ray camera 240 to selectively transmit the visible rays or the near-infrared rays.

In addition, the filter slide mount 220 can control the operation of the near-infrared cut-off filter 210. That is, the filter slide mount 220 drives the actuator 250 to cause the near-infrared cut-off filter 210 to be disposed or not to be disposed in front of the visible ray/near-infrared ray measurement unit 200, whereby it is possible to allow the visible rays and the near-infrared rays to be selectively transmitted.

Further, the imaging lens 230 may form the visible ray image and the near-infrared ray image. The image to be formed may be a near-infrared ray image filtered through a near-infrared cut-off filter 210, and a visible and near-infrared ray image not filtered through the near-infrared cut-off filter 210.

It is preferable that the imaging lens 230 is a lens on which anti-reflection coating is performed for a wavelength of 400 to 850 nanometers (nm), and is comprised so that 90 percent (%) or more of visible rays and near-infrared rays are transmitted.

Herein, the visible ray/near-infrared ray camera 240 may be a complementary metal oxide semiconductor (CMOS) camera. In addition, it is preferable that the visible ray/near-infrared ray camera 240 has a quantum efficiency of 50 percent or more for a visible optical signal having a wavelength of 400 to 700 nm, and a quantum efficiency of a percent or more for the near-infrared optical signal having a wavelength of 800 to 850 nm.

Figure 10:
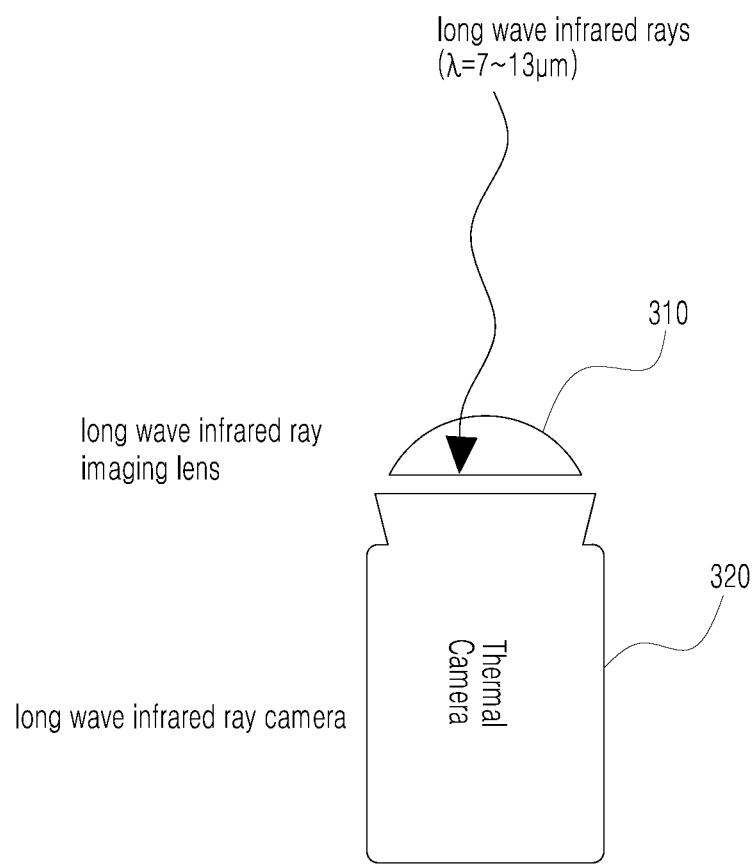
FIG. 10 is a diagram showing a long wave infrared ray measurement unit in a hybrid imaging system for photodiagnosis and phototherapy according to an embodiment of the present invention.

FIG. 10 is a diagram showing a long wave infrared ray measurement unit in a hybrid imaging system for photodiagnosis and phototherapy according to an embodiment of the present invention.

The long wave infrared ray measurement unit 300 measures the long wave infrared optical signal reflected from the light distribution unit 100. In addition, the long wave infrared ray measurement unit 300 may include a long wave infrared imaging lens 310 and a long wave infrared camera 320.

The long wave infrared imaging lens 310 may form an image of the long wave infrared optical signal reflected from the light distribution unit 100. The long wave infrared ray imaging lens 310 is made of any one of silicon, zinc selenide (ZnSe), and germanium so that the transmission is high for long wave infrared rays having a wavelength of 7 to 13 micrometers, and the anti-reflection coating may be added for a wavelength of 7 to 13 micrometers.

Further, the long wave infrared ray camera 320 may be a thermal imaging camera.

The light source unit 400 may irradiate the object 20 with near-infrared rays or long wave infrared rays having a predetermined wavelength. The light source unit 400 further includes a near-infrared light source 410 for irradiating the object 20 with a near-infrared optical signal and a long wave infrared light source 420 for irradiating the object 20 with a long wave infrared optical signal.

The light source unit 400 may further include a visible light source to irradiate the object 20 with visible rays.

The near-infrared light source 410 is preferably comprised to have a power of 1 W/cm$^2$ or more as a laser or LED light source having a predetermined bandwidth with a center wavelength of 808 nanometers (nm).

The control unit 500 may control the operation of the light distribution unit 100, the visible ray/near-infrared ray measurement unit 200, the long wave infrared ray measurement unit 300, and the light source unit 400.

Thus, the hybrid imaging system for photodiagnosis and phototherapy according to the present invention can acquire a visible ray and/or a near-infrared ray image and a long wave infrared ray image simultaneously without mutual distortion.

While the present invention has been particularly shown and described with reference to exemplary embodiments thereof, it is to be understood that the invention is not limited to the disclosed embodiments, but includes all modifications that are easily modified by those skilled in the art to which the present invention belongs.

DESCRIPTION ON REFERENCE NUMERALS OF DRAWINGS

10: hybrid imaging system 20: object
100: light distribution unit
110: transmissive layer
120: adhesive layer
130: long wave infrared ray reflective layer
200: visible ray/near-infrared ray measurement unit 210: near-infrared ray cut-off filter
220: filter slide mount
230: imaging lens
240: visible ray/near-infrared ray camera
250: actuator
300: long wave infrared ray measurement unit
310: long wave infrared imaging lens
320: long wave infrared ray camera
400: light source unit
410: near-infrared light source
420: long wave infrared light source
500: control unit

The invention claimed is:

1. A hybrid imaging system for photodiagnosis and phototherapy, which measures an optical signal generated from an object to simultaneously extract a visible ray image and a near-infrared ray (NIR) image, and a long wave infrared ray (LWIR: long wave infrared) image, the system comprising:
   a light source irradiating the object with near-infrared rays or long wave infrared rays having a predetermined wavelength;
   a light distribute transmitting or reflecting an optical signal generated according to a light source irradiated to the object from the light source unit to be distributed into a visible optical signal and a near-infrared optical signal, and a long wave infrared optical signal;
   a visible ray/near-infrared ray measure receiving and selectively filtering the visible optical signal and the near-infrared optical signal distributed from the light distributer unit, to measure at least one of the visible optical signal and the near-infrared optical signal; and
   a long wave infrared ray measurer unit receiving and measuring the long wave infrared optical signal distributed from the light distributer,
   wherein the visible ray/near-infrared ray measurer includes:
   a near-infrared ray cut-off filter provided at a front end of the visible ray/near-infrared ray measurer into which the optical signal is incident to selectively transmit only the near-infrared optical signal;
   a filter slide mount controlling an operation of the near-infrared ray cut-off filter;
   an imaging lens forming an image of the visible optical signal and/or the near-infrared optical signal; and
   a visible ray/near-infrared ray camera measuring the optical signal of which the image is formed through the imaging lens to extract a visible ray image and/or a near-infrared ray image.

2. The system of claim 1, wherein the light distributer unit includes:
   a transmissive layer through which the visible optical signal and the near-infrared optical signal of a predetermined wavelength are transmitted, and a long wave infrared ray reflective layer by which the long wave infrared optical signal is reflected.

3. The system of claim 2, wherein the transmissive layer comprises zinc selenide (ZnSe) so that the visible optical signal and the near-infrared optical signal having a wavelength of 400 to 850 nanometers (nm) are transmitted in an anti-reflection manner.

4. The system of claim 2, wherein the long wave infrared ray reflective layer comprises gold or platinum with high long wave infrared reflection.

5. The system of claim 2, wherein an adhesive layer is provided between the transmissive layer and the long wave infrared ray reflective layer to allow the transmissive layer and the long wave infrared ray reflective layer to adhere to each other, and
   the adhesive layer comprises indium tin oxide (ITO) or titanium.

6. The system of claim 1, wherein the long wave infrared ray measurer includes:
   a long wave infrared imaging lens receiving the long wave infrared optical signal distributed from the light distribution unit to form an image thereof, and a long wave infrared ray camera measuring the long wave infrared optical signal of which an image is formed through the long wave infrared imaging lens to extract the long wave infrared ray image.

7. The system of claim 6, wherein the long wave infrared imaging lens comprises at least one of silicon, zinc selenide (ZnSe), and germanium with high transmission for a long wave infrared ray having a wavelength of 7 to 13 micrometers.

* * * * *